United States Patent [19]
Borig et al.

[11] Patent Number: 4,777,941
[45] Date of Patent: Oct. 18, 1988

[54] ORTHOPEDIC KNEE PROSTHESIS AND HINGE

[76] Inventors: Donald A. Borig, 44 Pine Dr., Chester Springs, Pa. 19425; Godfrey Harris, 10676 W. Tufts Pl., Littleton, Colo. 80120; Gary P. Korngold, 3435 Fayance Pl., Thousand Oaks, Calif. 91362

[21] Appl. No.: 79,261

[22] Filed: Jul. 29, 1987

[51] Int. Cl.$^4$ .................................................. A61F 3/00
[52] U.S. Cl. ..................................... 128/80 C; 623/27; 623/59
[58] Field of Search ................ 403/117, 113, 102; 623/27, 39, 45; 128/80 C, 88, 77

[56] References Cited

U.S. PATENT DOCUMENTS

| | | | |
|---|---|---|---|
| 2,623,440 | 3/1953 | Hauser et al. | 128/80 |
| 2,753,864 | 7/1956 | Weidemann | 128/87 R |
| 2,857,783 | 10/1958 | Ranck et al. | 74/531 |
| 3,655,297 | 4/1972 | Boleu | 403/102 |
| 3,826,251 | 7/1974 | Ross | 128/80 |
| 3,863,274 | 2/1975 | Gladaszeushi | 623/45 |
| 3,993,056 | 11/1976 | Rabischong et al. | 128/89 R |
| 4,088,130 | 5/1978 | Applegatge | 128/80 F |
| 4,136,404 | 1/1979 | Lange | 128/80 |
| 4,145,766 | 3/1979 | May | 623/45 |
| 4,169,467 | 10/1979 | Rabischong et al. | 128/80 G |
| 4,249,524 | 2/1981 | Anderson | 128/88 |
| 4,310,932 | 1/1982 | Nader | 623/45 |
| 4,337,764 | 7/1987 | Lerman | 128/80 F |
| 4,370,977 | 2/1983 | Mauldin et al. | 128/80 F |
| 4,397,308 | 8/1983 | Hepburn | 128/88 |
| 4,467,792 | 8/1984 | Young et al. | 128/88 |
| 4,481,941 | 11/1984 | Rolfes | 128/87 R |
| 4,489,718 | 12/1984 | Martin | 128/88 |
| 4,502,472 | 3/1985 | Pansiera | 128/80 F |
| 4,520,802 | 6/1985 | Mercer | 128/80 C |
| 4,559,935 | 12/1985 | Young et al. | 128/88 |
| 4,599,998 | 7/1986 | Castillo | 128/80 C |
| 4,699,129 | 10/1987 | Aaserude | 128/80 C |

FOREIGN PATENT DOCUMENTS

| | | | |
|---|---|---|---|
| 1324883 | 12/1963 | France | |
| 2454295 | 12/1980 | France | 128/80 C |
| 2472375 | 7/1981 | France | 128/88 |
| 2130488 | 6/1984 | United Kingdom | |
| 2177603 | 1/1987 | United Kingdom | |
| 2182714 | 5/1987 | United Kingdom | |

OTHER PUBLICATIONS

Seton Products, Inc., Trade Literature for "Seton Masterhinge Adjustabrace," SET-1856-1585RP, 1985.
Rohr & Co., Hilden Rhld., Trade Literature for Hip Orthoses, not dated, Catalog.
Orthotics Division of Hosmer, Trade Literature for "Cerebral Palsy Orthosis Kit" and "Post-Op Total Hip Orthotic Joint," pp. 0-9 and 0-10.

*Primary Examiner*—Richard J. Apley
*Assistant Examiner*—James Prizant
*Attorney, Agent, or Firm*—Woodcock Washburn Kurtz Mackiewicz & Norris

[57] ABSTRACT

An orthopedic hinge is provided for controlling the flexion and extension of an associated body part, for example, a knee or elbow. The hinge employs a housing connected to a pair of control arms which are rotatably mounted to the housing and are free to move independently of one another. The hinge also includes a first and a second adjustment means having single elements for simultaneously controlling both control arms to thereby define an arc of extension and an arc of flexion of the body part. The hinge preferably includes a single screw for blocking the extension of the joint and a single screw for setting the flexion of the joint. The hinge can be adjusted for free motion throughout a preferred 120° range of motion and can be selectively locked at any point within this range.

19 Claims, 3 Drawing Sheets

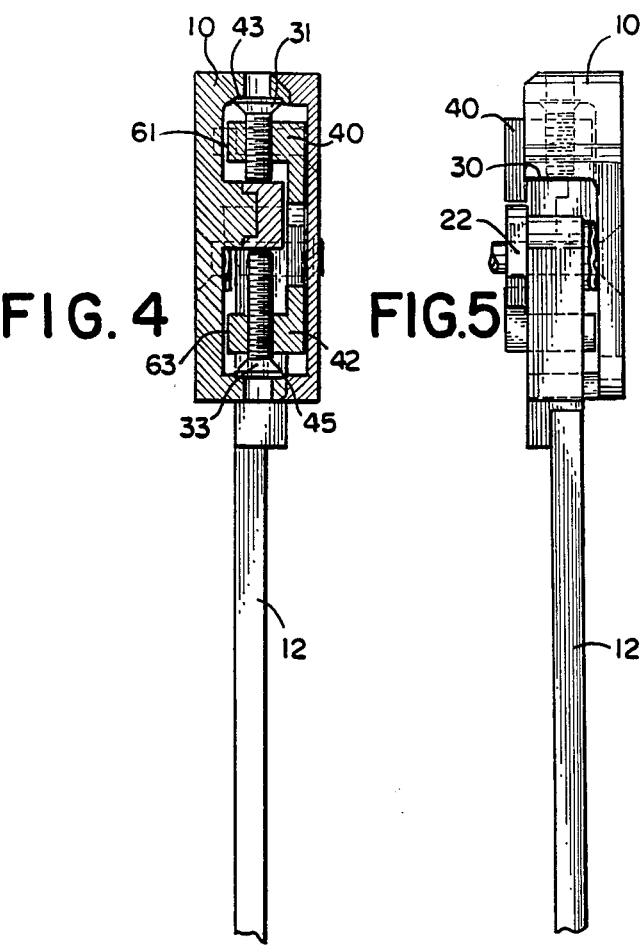

ORTHOPEDIC KNEE PROSTHESIS AND HINGE

FIELD OF THE INVENTION

This invention relates to orthosis for regulating the movement of an associate body part and in particular, to orthopedic knee and elbow hinges providing facilitated adjustment to the arc of flexion and extension.

BACKGROUND OF THE INVENTION

Traditionally, orthopedic hinges were of two types, polycentric and single pivotal. Single pivot hinges permit changes in the flexion and extension angles when the pivot axis of the hinge and that of the limb are aligned. However, when these axes are not aligned, these devices apply a force or bending moment to the joint that can be both painful and deleterious to the success of orthopedic implants and other corrective surgery.

Polycentric prostheses usually consist of two control arms having separate pivot points. See Castillo, U.S. Pat. No. 4,599,998, which is incorporated by reference. The control arms of Castillo operate through identical arcs of rotation and are mutually dependent on the same activation member. Castillo discloses an adjustable polycentric orthopedic appliance hinge having a rack cooperating with pinions formed at the ends of a pair of control arms. The device engages the arms in dependent relation with one another and with a drive member such that the rotational position of the arms, and thus the angle between them, is altered, upon translation of the drive member. The drive member of this device is combined with stops that limit the degree of the translation of the drive member in at least one direction and, preferably, in both directions. The stops are independently adjustable to provide a range of angular movement to the control arms.

Devices such as that disclosed by Castillo have multi-hinge pivot points, however, there are frictional and bending forces created at the contact point between the teeth of the control arms and the drive member. These forces are translated to the joint and complicate the "tracking", or alignment with the joint. Moreover, when the control arms contact a stop point for either flexion or extension, the dependent engagement of the arms with the drive member creates stresses which can result in forward or backward pressure at the joint with attendant consequences.

Freely, bi-pivotal prostheses, on the other hand, provide a greater distance between their pivot points, leaving a margin of error for positioning the knee within the appliance without creating bending moments at the knee joint. See Seton Products Inc., trade literature SET-1856-1585 RP disclosing the MASTER HINGE ® brace. Bi-pivotal motion provides improved knee tracking by permitting changes in the angle between the control arms when the knee joint proceeds to a point at which the pivot points of the hinge and the joint are no longer aligned. The MASTER HINGE ® design is positively adjustable for controlling extension and flexion of the knee.

Despite its advantages, the MASTER HINGE ® provides a complicated arrangement of two adjustment screws for each control arm for independently setting the extension and flexion arc of each arm. The hinge provides no mechanism for matching the flexion or extension of both arms simultaneously and relies on the skill and patience of a physician to match the arcs of restriction of the upper and lower control arms. Generally, if a mistake is made in matching the arcs and they are adjusted to be unequal, more stress will be created at the joint.

It is further understood that physicians cannot readily determine what range of motion is provided by the arms without moving the arms about their pivots over their entire arc. This procedure takes considerably more time and requires a longer training period for acquainting physicians with its use. In fact it is understood that, one of the most common complaints provided by physicians using this device is that the product is too complicated to learn and use on a regular basis.

Accordingly, there is a need for an orthopedic hinge that provides joint tracking capability while at the same time providing for matched arcs for flexion and extension of the control arms. There is also a need for an orthopedic hinge that is freely bi-pivotal, which also provides a less complicated adjustment means for varying the range of motion of the control arms.

SUMMARY OF THE INVENTION

An orthopedic hinge is provided having control arms which are free to rotate independent of one another. The hinge also includes a first and second adjustment means for simultaneously controlling each of the control arms to thereby define an arc of extension and an arc of flexion of an associated body part. Each of the control arms of this device have an arc of travel of about 30° to 120°, preferably 40° to 80°, and more preferably about 60°. This arc is ultimately limited by interfering portions of the preferred hinge housing. The device includes a preferred single adjustment screw for controlling the arc of flexion of both arms, and a preferred single adjustment screw for controlling the arc of extension of both arms. The preferred screws are preferably disposed in threaded engagement with wedge portions which are caused to move longitudinally along the screw. These wedge portions can be engaged with the control arms and moved along the screw because they contact the walls of the housing to preclude their rotation with the screws. Preferably, as the wedges move towards the center line defined by a pair of pivot points of said control arms, the degree of extension and flexion permitted by these control arms becomes reduced by reason of interference between the wedges and the control arms.

It is, therefore, an object of this invention to provide an orthopedic hinge that minimizes bending moments created at joints due to misalignment of the alignment centers of the hinge and the joint.

It is another object of this invention to provide an orthopedic hinge which is easier to use, and which can provide a reading for flexion setting and extension setting without undue experimentation.

It is still another object of this invention to provide an orthopedic hinge that provides for matched arcs of rotation for both control arms while still providing for independent movement of the control arms within a given range of arc mobility.

With these and other objects in view, which will become apparent to one skilled in the art as the description proceeds, this invention resides in the novel construction, combination, arrangement of parts and methods substantially as hereinafter described and more particularly defined in the attached claims.

BRIEF DESCRIPTION OF THE DRAWINGS

The accompanying drawings illustrate a complete embodiment of the invention according to the best mode for the best practical application of the principles thereof, and in which:

FIG. 4: is a transverse cross-sectional view of the embodiment of FIG. 2, taken through line 4—4 illustrating the preferred adjustment screws and wedges of this invention;

FIG. 5: is a transverse view of the orthopedic hinge of FIG. 3, illustrating how one of the control arms impinges a wedge for creating flexion block.

DESCRIPTION OF THE INVENTION

According to this invention, an orthopedic hinge is provided comprising a housing, a pair of control arms rotatably mounted to the housing which are free to move independently of one another, a first adjustment means for simultaneously controlling these control arms to thereby define an arc of flexion and a second adjustment means for simultaneously controlling the control arms to thereby define an arc of extension. The invention preferably utilizes only two adjustment screws, one for regulating the arc of extension and one for regulating the arc of flexion of an associated body part. Preferably, the orthopedic hinge of this invention includes a scale on the housing which in conjunction with indicator means on the preferred wedges, provides a reading indicative of the degree of "flexion control" and "extension block" of the hinge.

Referring now to the Figures, a preferred hinge embodiment 100 is provided. A housing 10, preferably constructed of stainless steel, and preferably AISI 303 stainless steel is depicted. The housing 10 is preferably constructed with a face plate. The housing 10 and face plate ideally are made from investment castings to provide a greater degree of accuracy of movement of the hinge 100.

Figure 1:
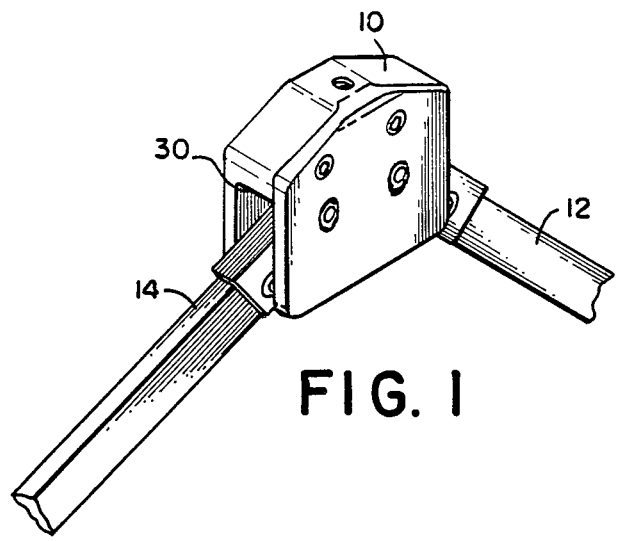
FIG. 1: is a perspective drawing of the orthopedic hinge of this invention.
Figure 3:
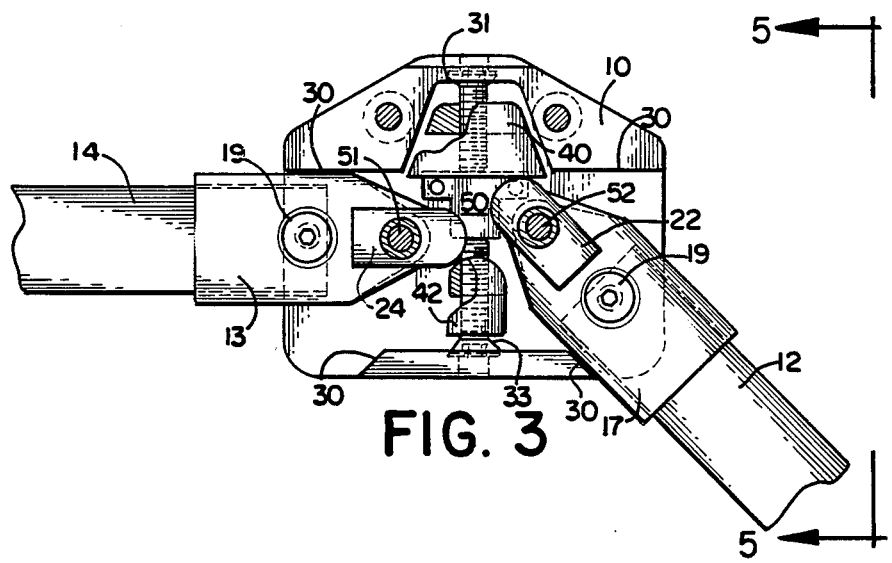
FIG. 3: is a enlarged, cross-sectional view taken through line 3—3 of FIG. 2, illustrating the internal elements of the orthopedic hinge of FIG. 1 including cut away views of the wedge portions of this embodiment.

As illustrated in FIGS. 1 and 3, a pair of control arms 12 and 14 are rotatably mounted to the housing 10. The control arms 12 and 14 are free to move independently of one another with unimpinged bi-polar movement between the interfering portions 30. This invention includes a first adjustment means having a first element for simultaneously controlling the pair of control arms 12 and 14 to thereby define an arc of flexion of an associated body part. Also included is a second adjustment means having a second element for simultaneously controlling the pair of control arms 12 and 14 to thereby define an arc of extension of the body part. Interfering portions 30, which are preferably an integral part of the housing 10, are designed to limit the maximum arc of rotations for each of the control arms 12 and 14.

Further according to this invention, the first element of the first adjustment means can comprise a first single adjustment screw 31 for adjusting an arc of rotation of the pair of control arms 12 and 14 during flexion of the body part. The first adjustment means can also comprise a first wedge portion 40 within the housing 10 for engaging and limiting the arc of rotation of the pair of control arms 12 and 14 during flexion of the body part.

The second adjustment means of this invention preferably comprises a second single adjustment screw 33 for adjusting an arc of rotation of the pair of control arms 12 and 14 during extension. The second adjustment means can further comprise a second wedge portion 42 within the housing 10 for engaging and limiting the arc of rotation of the pair of control arms 12 and 14 during extension. As in the case of the housing 10, these wedge portions 40 and 42 are preferably investment cast from AISI 303 stainless steel.

As described in FIG. 4, the preferred arrangement of the hinge includes the first wedge portion 40 disposed in threaded engagement with the first single adjustment screw 31 and the second wedge portion 42 disposed in threaded engagement with the second single adjustment screw 33. The control arms 12 and 14 of this invention are preferably freely bi-pivotal. By this, it is meant that the first arm 14 of said pair of control arms rotates about a first pivot point 51 and the second arm 12 rotates about a second pivot point 52. The first and second pivot points 51 and 52 are preferably located within the housing 10. Ideally, the first and second adjustment screws 31 and 33 are located along an axis bisecting the first and second pivot points 51 and 52.

As depicted FIG. 3, control arms 12 and 14 preferably are constructed with arm holding castings 13 and 17 for engaging the first and second wedge portions 40 and 42. These castings 13 and 17 are preferably AISI 303 stainless steel investment castings and are fastened to control arms 12 and 14 with fasteners 19, which are preferably stainless steel rivets. The control castings 13 and 17 preferably comprise projections 22 and 24 for engaging the first and second wedge portions 40 and 42, as substantially described in FIGS. 3 and 5.

In order to minimize the weight of the overall hinge 100, the arms 12 and 14 can be constructed of light weight metal, such as aluminum or magnesium, preferably 6061 aluminum in a T-6 heat-treated condition. The arms 14 and 17, once positioned in the preferred control castings 13 and 17, are free to rotate about pivot points 51 and 52.

Further according to FIG. 3, a block member 50 is provided which can be attached to an interior portion of the housing 10 for engaging with the end portions of the first and second single adjustment screws 31 and 33. Preferably the block 50 is disposed so that the first and second wedge portions 40 and 42 slidably overlap its top surface. This is not a requirement, however, this arrangement may provide more stability to the wedges 40 and 42 when adjusted by screws 31 and 33.

Figure 2:
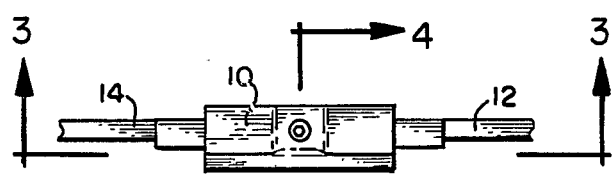
FIG. 2: is a top view of the orthopedic hinge of FIG. 1.

Referring again to FIG. 4, illustrating a cross-sectional view of the hinge 100 of FIG. 2, the operation of the adjustment screws 31 and 33 can now be explained. According to one embodiment of this invention, the head portion of each of the screws is disposed in complementary formed regions 43 and 45 of the hinge housing 10 such that a rotation of the screws 31 and 33 does not result in a longitudinal translation of the screws 31 and 33 within the housing 10. Also according to this embodiment, the first and second wedge portions 40 and 42 can comprise a surface 61 or 63 for engaging with the housing 10 and for preventing a rotation of the first and second wedge portions 40 and 42 when the screws 31 and 33 are rotated. In accordance with the preferred teachings of this invention, the first adjustment screw 31 causes a longitudinal translation of the first wedge portion 40 along said first adjustment screw 31. This translation causes a change in the arc of rotation of both control arms 12 and 14 during flexion of an associated body part. Also preferred, but not necessarily required, is the feature that the second adjustment screw 33 cause a longitudinal translation of the second wedge portion 42 along the second adjustment screw 33 to cause a change in the arc of rotation of both control arms 12 and 14 during extension of the body part.

Figure 6:
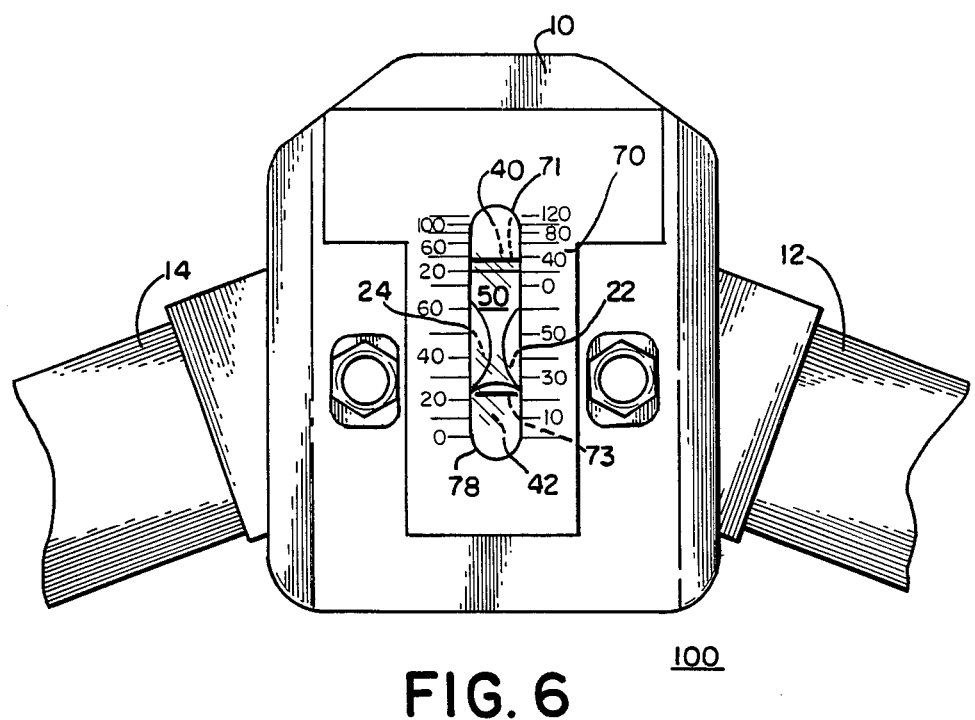
FIG. 6: is an enlarged view of the hinge embodiment of FIG. 1 illustrating the preferred scale and indicator means for determining the setting of the device.

Referring now to FIG. 6, a novel flexion-extension gauge is provided. In the preferred embodiment, the housing 10 comprises an aperture or calibration window 78 for observing a position within said housing for said wedge portions 40 and 42. The wedge portions can be provided with indicator means, shown as black lines 71 and 73 for providing an indication of the longitudinal translation of said wedge portions 40 and 42 within said housing 10. In the most preferred embodiment, the housing comprises scale means 70 which in conjunction with the indicator means 71 and 73 provides a reading indicative of an adjusted arc of rotation for both control arms 12 and 14 during flexion and extension of the associated body part.

In the most preferred embodiment of this invention, the first and second adjustment screws 31 and 33 have hexagonal heads adapted for an allen wrench. The invention is used by first inserting a supplied allen wrench into the first adjustment screw 31, corresponding to the "flexion control" of the device. The first adjustment 31 screw should be turned counter-clockwise until it stops. This process should be repeated with the second adjustment screw 33 corresponding to the "extension block" of the device. This setting will allow the hinge 100 to move unrestricted through about a preferred 120° range of motion.

To block extension, the supplied allen wrench, in the most preferred embodiment, is inserted into the second adjustment screw 33 and turned clockwise until the preferred black line marking, 71 on wedge portion 40 is observed through aperture or window 78 to align with a desired degree of setting on the scale means 70. To set inflexion, the supplied allen wrench is inserted into the second adjustment screw 33 and turned clockwise until the preferred black line, corresponding to marking 73 on wedge portion 42, aligns with a desired degree of setting on said scale means 70. Similarly, by turning the appropriate adjustment screw counter-clockwise the settings for flexion or extension can be reduced until a new desired setting is achieved.

To lock the hinge 100 in a fixed position, a desired degree of extension block must be set, as described above. Then the first adjustment screw 31 corresponding to flexion control, is turned clockwise until it stops. One must not over-tighten the screws 31 and 33 once the hinge 100 has been locked, in order to avoid damaging the hinge 100. The hinge 100 can be unlocked by simply turning the first and second adjustment screws 31 and 33 counter-clockwise.

From the foregoing it can be realized that this invention provides an improved orthopedic hinge having independently bi-pivotal control arms and greatly facilitated adjustment means. Although various embodiments have been illustrated, this was for the purpose of describing but not limiting the invention. Various modifications, which will become apparent to one skilled in the art, are within the scope of this invention described in the attached claims.

We claim:

1. An orthopedic hinge for limiting the flexion and extension of an associated body part, comprising:
    (a) a housing;
    (b) a pair of control arms rotatably mounted to said housing, said control arms being free to move independently of one another;
    (c) first adjustment means having a first element for simultaneously limiting said pair of control arms to thereby define an arc of flexion of said body part; and
    (d) second adjustment means having a second element for simultaneously limiting said pair of control arms to thereby define an arc of extension of said body part.

2. The hinge of claim 1, wherein said housing comprises interfering portions for limiting a maximum arc of rotation for each of said control arms.

3. The hinge of claim 2, wherein said first element comprises a first single adjustment screw for adjusting an arc of rotation of said pair of control arms during flexion of the body part.

4. The hinge of claim 3, wherein said first adjustment means further comprises a first wedge portion within said housing for engaging and limiting the arc of rotation of said pair of control arms during flexion of the body part.

5. The hinge of claim 4, wherein said second adjustment means comprises a second single adjustment screw for adjusting an arc of rotation of said pair of control arms during extension of the body part.

6. The hinge of claim 5, wherein said second adjustment means comprises a second wedge portion within said housing for engaging and limiting the arc of rotation of said pair of control arms during extension of the body part.

7. The hinge of claim 6, wherein said first wedge portion is disposed in threaded engagement with said first single adjustment screw and said second wedge portion is disposed in threaded engagement with said second single adjustment screw.

8. The hinge of claim 1, wherein a first arm of said pair of control arms rotates about a first pivot point and a second arm of said pair of control arms rotates about a second pivot point, said first and second pivot points being located within said housing.

9. The hinge of claim 8, wherein said first and second adjustment screws are located along an axis bisecting said first and second pivot points.

10. The hinge of claim 9, further comprising a block member attached to an interior portion of said housing for engaging with an end portion of said first and second single adjustment screws.

11. The hinge of claim 10, wherein the head portion of each of said screws is disposed in complementary formed regions of said hinge housing such that a rotation of said screws does not result in a longitudinal translation of said screws within said housing.

12. The hinge of claim 11, wherein said first and second wedge portions comprise a surface for engaging said hinge housing and for preventing a rotation of said first and second wedge portions when said screws are rotated.

13. The hinge of claim 12, wherein a rotation of said first adjustment screw causes a longitudinal translation of said first wedge portion along said first adjustment screw, said translation causing a change in the arc of rotation of said pair of control arms during flexion of the body part.

14. The hinge of claim 13, wherein a rotation of said second adjustment screw causes a longitudinal translation of said second wedge portion along said second adjustment screw, said translation causing a change in the arc of rotation of said pair of control arms during extension of the body part.

15. The hinge of claim 14, wherein said first and second wedge portions comprise a portion which overlaps said block member.

16. The hinge of claim 15, wherein said pair of control arms comprise projections for engaging said first and second wedge portions.

17. The hinge of claim 13, wherein said housing comprises an aperture for permitting the observation of a position within said housing for said wedge portions.

18. The hinge of claim 17, wherein said wedge portions are provided with indicator means for providing an indication of the longitudinal translation of said wedge portions within said housing.

19. The hinge of claim 18, wherein said housing comprises scale means which in conjunction with said indicator means provides a reading indicative of an adjusted arc of rotation for said pair of control arms during flexion and extension of the body part.

* * * * *